United States Patent [19]

Cullen

[11] 4,156,096

[45] May 22, 1979

[54] PROCESS FOR RECOVERING DISSOLVED IMINODIACETONITRILE FROM EFFLUENT LIQUORS

[75] Inventor: Barry A. Cullen, Nashua, N.H.

[73] Assignee: W. R. Grace & Co., New York, N.Y.

[21] Appl. No.: 886,934

[22] Filed: Mar. 15, 1978

[51] Int. Cl.$^2$ ............... C07C 121/43; C07C 99/12
[52] U.S. Cl. ............... 562/571; 260/465.5 A; 260/465.5 R
[58] Field of Search ............... 260/465.5 R, 465.5 A; 562/571

[56] References Cited

U.S. PATENT DOCUMENTS

| | | | |
|---|---|---|---|
| 2,511,487 | 6/1950 | Thompson | 260/465.5 A |
| 3,904,668 | 9/1975 | Gaudette et al. | 260/465.5 A |
| 3,950,384 | 4/1976 | Neumaier et al. | 260/465.5 A |
| 3,988,360 | 10/1976 | Gaudette et al. | 260/465.5 A |
| 3,993,681 | 11/1976 | Cullen | 260/465.5 R X |

*Primary Examiner*—Joseph Paul Brust
*Attorney, Agent, or Firm*—Elton Fischer; Phillip M. Pippinger

[57] ABSTRACT

A process for recovering iminodiacetonitrile (IDAN) values from an aqueous IDAN solution comprising: (a) extracting the aqueous IDAN solution with methylene chloride to dissolve a portion of IDAN in the methylene chloride to form a methylene chloride solution of IDAN; and (b) separating and recovering the IDAN values from the methylene chloride.

In an alternative embodiment the IDAN values can be separated from the methylene chloride solution of IDAN by extracting the methylene chloride solution with an aqueous alkali metal hydroxide solution to form water-soluble dialkali metal iminodiacetate (IDAM$_2$ wherein M is an alkali metal cation) which remains in the aqueous alkali metal hydroxide solution. The IDAM$_2$ can be recovered from the alkali metal hydroxide solution by conventional methods (e.g., by treating with a strong acid to precipitate iminodiacetic acid (IDA)).

Each extraction (the extraction with methylene chloride and the extraction with aqueous alkali metal hydroxide solution) can be conducted as a batchwise extraction or as a continuous counter-current extraction.

4 Claims, No Drawings

PROCESS FOR RECOVERING DISSOLVED IMINODIACETONITRILE FROM EFFLUENT LIQUORS

BACKGROUND OF THE INVENTION

Iminodiacetonitrile (IDAN) is an intermediate in a route to iminodiacetic acid (IDA). IDAN can be formed by: (a) reacting ammonia, formaldehyde, and HCN; or (b) hexamethylenetetramine and HCN; or (c) glycolonitrile and ammonia in an aqueous medium. The resulting IDAN is then hydrolyzed in a hydrolysis step with an aqueous alkali metal hydroxide solution to form an alkali metal salt of iminodiacetic acid, IDA, (i.e., IDAM$_2$ in which M is an alkali metal ion provided by the alkali metal hydroxide (e.g., IDANa$_2$ where using sodium hydroxide as the alkali metal hydroxide)) which is acidified (generally with sulfuric acid or hydrochloric acid) in an acidification step to form IDA which will precipiatate as solid IDA. The solid IDA can be separated and recovered.

In such synthesis an effluent stream (an aqueous solution) generally containing about 0.1-10% IDAN may be encountered. The process of this invention can be used to recover IDAN values from such effluent stream to decrease the loss of a valuable intermediate and to eliminate or substantially eliminate a potential pollution source (the IDAN present in the effluent stream).

The fact that methylene chloride, an organic solvent which is substantially insoluble in water, can be used to extract IDAN from an aqueous solution containing a relatively low concentration of IDAN is surprising because U.S. Pat. No. 3,463,811, Godfrey et al, teaches that an admixture of kerosene (an organic solvent which is substantially insoluble in water) and a kerosene-soluble substantially water-insoluble amine failed to extract any appreciable amount of nitrilotriacetonitrile (NTAN) from an aqueous system comprising both dissolved and solid phase NTAN.

The respective formulas of IDAN and NTAN are:

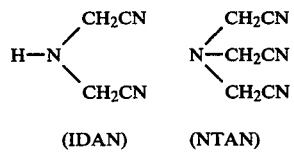

(IDAN)     (NTAN)

Liquid-liquid extraction, which is generally called "liquid extraction" or "solvent extraction", is well known to those skilled in the art. It is taught by Perry and Chilton, "Chemical Engineers' Handbook," 5th Edition, McGraw-Hill Book Company, New York, N.Y., pages 15-2 and 15-3 (1973).

SUMMARY OF THE INVENTION

In summary, this invention is directed to a process for separating and recovering iminodiacetonitrile (IDAN) values from an aqueous IDAN solution, said process comprising:
(a) extracting the aqueous IDAN solution with methylene chloride to transfer IDAN from the aqueous IDAN solution to the methylene chloride and separating the methylene chloride which now contains a portion of the IDAN from the resulting extracted aqueous IDAN solution; and
(b) separating the IDAN from the methylene chloride (e.g., by evaporating the methylene chloride to leave IDAN which can be recovered; the evaporated methylene chloride can also be recovered).

The extraction can be conducted as a batchwise extraction or as a continuous counter-current extraction.

DESCRIPTION OF OTHER EMBODIMENTS

In the process of the above Summary:
1. The volume ratio of aqueous iminodiacetonitrile solution to methylene chloride at the start of the extraction is about 1:0.1-10.
2. The contact time between the aqueous iminodiacetonitrile solution and the methylene chloride during the extraction is about 0.1-10 minutes.
3. Iminodiacetonitrile is separated from the methylene chloride solution of iminodiacetonitrile by evaporating methylene chloride therefrom.

In another embodiment ("Embodiment A") this invention is directed to a process for recovering IDAN values from an aqueous iminodiacetonitrile solution, said process comprising:
(a) extracting the aqueous iminodiacetonitrile solution with methylene chloride in a first extraction to form: (i) a solution of iminodiacetonitrile in the methylene chloride; and (ii) an extracted aqueous iminodiacetonitrile solution;
(b) separating the solution of iminodiacetonitrile in methylene chloride from the extracted aqueous iminodiacetonitrile solution;
(c) extracting the solution of iminodiacetonitrile in the methylene chloride with an aqueous solution of an alkali metal hydroxide in a second extraction to remove iminodiacetonitrile values from the methylene chloride and to form: (i) an aqueous solution of a dialkali metal salt of iminodiacetic acid (IDAM$_2$) by hydrolyzing (saponifying) the IDAN to IDAM$_2$ substantially as it (the IDAN) is extracted from the solution of IDAN in the methylene chloride; and (ii) extracted methylene chloride;
(d) separating the aqueous solution of dialkali metal salt of iminodiacetic acid from the extracted methylene chloride; and
(e) recovering the aqueous solution of the IDAM$_2$ (e.g., by placing the aqueous solution of said alkali metal salt in the hydrolysis step or in the acidification step in the above-mentioned route to IDA).

In other embodiments of the process of Embodiment A:
1. The aqueous solution of dialkali metal iminodiacetate is treated with sulfuric acid or hydrochloric acid to convert the dialkali metal iminodiacetate to iminodiacetic acid which precipitates and is recovered.
2. The volume ratio of aqueous alkali metal hydroxide solution to methylene chloride is about 1:0.1-10.
3. Contact time between the aqueous alkali metal hydroxide solution and the solution of iminodiacetonitrile in methylene chloride is about 0.1-20 minutes.
4. The aqueous alkali metal hydroxide solution is sodium hydroxide.
5. The mole ratio of alkali metal hydroxide to the iminodiacetonitrile present in the solution of iminodiacetonitrile in methylene chloride is at least 1.

Each extraction (i.e., the extraction of the aqueous IDAN solution with methylene chloride and the extraction of the methylene chloride solution of IDAN with aqueous alkali metal hydroxide) can be conducted batchwise or as a continuous counter-current extraction.

DETAILED DESCRIPTION OF THE INVENTION

While the process of this invention is especially valuable for separating and recovering IDAN from aqueous effluent liquors containing about 1–5% IDAN, it is operable with aqueous solutions having higher or lower concentrations of IDAN.

Because of this disclosure it will be readily apparent to those skilled in the art that, where operating at atmospheric pressure, at elevated pressure, or at reduced pressure, the extraction temperature for each extraction (i.e., the extraction of IDAN from the aqueous IDAN solution with methylene chloride and the extraction of IDAN values from the methylene chloride solution of IDAN with aqueous alkali metal hydroxide solution) should be below the boiling point of methylene chloride at the extraction pressure.

Extraction temperatures of about 0°–38° C. are operable for each extraction at about atmospheric pressure but a temperature of about 20°–38° C. is generally preferred.

As noted supra, each extraction (i.e.: (a) the first extraction wherein IDAN is extracted from the effluent stream by the methylene chloride; and (b) the second extraction wherein IDAN values are extracted from the methylene chloride by the aqueous alkali metal hydroxide solution) can be conducted as a continuous extraction (e.g., by: (a) passing the methylene chloride and the aqueous IDAN solutions through a tube or column in counter-current flow; and (b) passing the solution of IDAN in methylene chloride and the aqueous solution of the alkali metal hydroxide through a tube or tower in counter-current flow) or as a batch extraction. The first extraction can be a continuous extraction while the second is a batch extraction or vice versa.

It is sometimes preferable (especially where using a batch extraction method) to run two or more first extractions in series (i.e., where extracting IDAN from an effluent stream with methylene chloride). In other words, the extracted aqueous IDAN solution from one extraction can be submitted to a second similar extraction with a fresh lot of methylene chloride (i.e., methylene chloride which is substantially free of IDAN) and the twice-extracted aqueous IDAN solution from this extraction can be submitted to a further extraction with a fresh lot of methylene chloride. This procedure (series of extractions) can be continued until the IDAN content of the aqueous IDAN solution from the final extraction has been reduced to a predetermined level.

Where using a series of batch first extractions to transfer IDAN from the first aqueous IDAN solution which can be an effluent liquor to the methylene chloride, counter-current type flow of the methylene chloride can be used. In other words, where using a series of four first extractions—i.e., Extractions A, B, C, and D in which IDAN is extracted from a batch of effluent solution with methylene chloride: (a) methylene chloride which is free of IDAN or substantially free of IDAN can be used in Extraction D; (b) the methylene chloride containing the IDAN extracted in Extraction D can be used in Extraction D; (c) the methylene chloride containing the IDAN extracted in Extraction D and C can be used in Extraction B; and (d) the methylene containing IDAN from Extractions D, C, and B can be used in Extraction A. IDAN can then be recovered from the methylene chloride used in Extraction A, and the resulting IDAN-free or substantially IDAN-free methylene chloride can be recovered and reused in a replication of Extractions D, C, B and A. As used herein, the term "Extraction A" means the extraction performed on a fresh stream of aqueous IDAN solution which has not previously been extracted, the term "Extraction B" means the extraction performed on the aqueous IDAN solution which had been extracted in the above-defined Extraction A, the term "Extraction C" means the extraction which is performed on the aqueous IDAN solution which had been extracted in the above-defined Extractions A and B, and the term "Extraction D" means the extraction which is performed on the aqueous IDAN solution which had been extracted in the above-defined Extractions A, B, and C.

It will be readily apparent to those skilled in the art that, where starting a series of batch extractions (e.g., Extractions A, B, C, and D) using such counter-current type flow for the first time, there will be no aqueous IDAN solutions which have been submitted to Extractions A, B, and C for use in Extractions D, C, and B. Accordingly, if desired, such aqueous IDAN solutions can be simulated by diluting portions of the starting IDAN solution (e.g., a plant effluent stream or other fresh IDAN primary liquor of the general type described in the first paragraph of the Example, infra). Alternatively, starting Extractions D, C, B, and A can each be run using an undiluted fresh IDA primary liquor which can be an effluent stream from the IDAN unit of an IDAN/IDA plant. A replication can then be run in which: (a) Extraction D is repeated by extracting the aqueous IDAN solution from previous Extraction C with methylene chloride which is free or substantially free of IDAN; (b) Extraction C is repeated by extracting the aqueous IDAN solution from previous Extraction B with the methylene chloride from repeated Extraction D; (c) Extraction B is repeated by extracting the aqueous IDAN solution from previous Extraction A with methylene chloride from repeated Extraction C; and (d) Extraction A is repeated by extracting a portion of fresh IDAN primary liquor with methylene chloride from repeated Extraction B. IDAN can be recovered from the methylene chloride from repeated Extraction A, and the resulting IDAN-free or substantially IDAN-free methylene chloride can be recovered and reused in another replication.

One extraction is sufficient where using either a batch or a continuous extraction method in the second extraction wherein IDAN values are extracted from the solution of IDAN in methylene chloride with an aqueous solution of an alkali metal hydroxide whereby the IDAN is extracted from the methylene chloride by the aqueous alkali metal hydroxide solution and converted to an aqueous solution of IDAM$_2$ as represented by the equation:

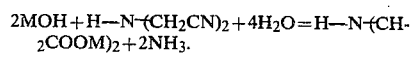

While the ratio (volume ratio) of aqueous iminodiacetonitrile solution to methylene chloride used in the process of this invention is not critical, ratios of 1:0.1–10 are operable and ratios of 1:0.5–2 are generally preferred. Said ratio is inversely proportional to the volume of methylene chloride used per unit volume of the aqueous IDAN solution. Doubling the volume of methylene chloride per unit volume of aqueous IDAN solution cuts the ratio in half.

Sodium hydroxide is a preferred alkali metal hydroxide for use in the process of this invention. However, potassium hydroxide and lithium hydroxide are operable.

Contact time in the first extraction (where transferring IDAN from the aqueous stream to the methylene chloride) is not critical. A contact time of 0.1–10 minutes is generally preferred where using a batch extraction technique and 0.1–10 minutes where using a continuous extraction technique; however, shorter and longer contact times are operable.

Contact time in the second extraction (where transferring IDAN values from the methylene chloride solution of IDAN to the aqueous alkali metal hydroxide solution) should be sufficient to remove all or substantially all of the IDAN from the methylene chloride. Contact times of 1–20 minutes are generally preferred where using a batch extraction technique and contact times of 1–20 minutes are generally preferred where using a continuous extraction technique; however, shorter and longer contact times are operable.

It is preferred in the second extraction (the extraction in which IDAN values are extracted from the methylene chloride solution of IDAN with an aqueous alkali metal hydroxide solution) that the aqueous alkali metal hydroxide solution contain sufficient alkali metal hydroxide to saponify (hydrolyze) all or substantially all of the IDAN present in the methylene chloride solution which is being extracted. This is, as will be readily apparent to those skilled in the art, a function of both the volume ratio of alkali metal hydroxide solution to solution of IDAN in the methylene chloride solution and the respective concentrations (i.e., the concentration of: (a) the alkali metal hydroxide in the aqueous alkali metal hydroxide solution; and (b) the concentration of IDAN in the solution of IDAN in the methylene chloride).

The concentration of the alkali metal hydroxide in the aqueous alkali metal hydroxide solution used to remove IDAN from the solution of IDAN in the methylene chloride solution the second extraction is not critical. A concentration of about 0.5–5 moles per liter is generally preferred; however, higher and lower concentrations are operable. Where using lithium hydroxide, care should be used to avoid forming a saturated solution of LiOH. (The solubility of LiOH in water is about 17 g per 100 g of water at 100° C. and about 13 g per 100 g of water at 0° C.). Because of the far greater solubilities of sodium hydroxide and potassium hydroxide in water, it is easy to avoid the formation of saturated solutions of NaOH or KOH because there is no reason to operate near the saturation concentration of either of these bases (NaOH or KOH).

The instant invention will be better understood by referring to the following specific but nonlimiting example which was actually run. It is understood that said invention is not limited by said example which is offered merely to illustrate said invention. It is also understood that modifications can be made without departing from the spirit and scope of the invention.

EXAMPLE

Fresh IDAN primary liquor (1500 ml, 1655 g) containing 2.98% IDAN by weight was extracted with methylene chloride (1500 ml, 2002.5 g) at room temperature to remove a portion of the IDAN. The methylene chloride was then extracted with 1500 g of an aqueous 10% caustic soda (NaOH) solution at room temperature to convert the IDAN to water soluble $IDANa_2$ and to remove the resulting $IDANA_2$ from the methylene chloride. The resulting IDAN-free methylene chloride was reused to reextract the once-extracted primary liquor, and the process was repeated reusing in each instance the NaOH solution from the previous extraction until the primary liquor and methylene chloride had each been extracted four times.

Small samples (about 1.5 g) of: (a) the unextracted primary liquor; and (b) the fully extracted liquor were each diluted to 100 ml with water and made alkaline with 50% NaOH (about 1 g). After standing at room temperature for several hours the resulting alkaline solutions were analyzed for $IDANa_2$ and for $NTANa_3$. (The $NTANa_3$ resulted from IDAN and a small amount of glycolonitrile present in the IDAN primary liquor.)

Samples of the NaOH solution which had been used to extract $IDANa_2$ from the IDAN-containing methylene chloride were also analyzed for $IDANa_2$ and $NTANa_3$ after each extraction.

Before extraction the IDAN primary liquor contained 2.98% IDAN (corresponding to 49.3 g of IDAN) and no NTAN. After the fourth extraction with methylene chloride, the IDAN primary liquor contained 0.28% IDAN (corresponding to 4.6 g of IDAN). The NaOH solution contained 3.0% $IDANa_2$ (corresponding to 24.2 g IDAN) and less than 0.1% $NTANa_3$ after the first extraction, 4.34% $IDANa_2$ (corresponding to 24.2 g IDAN) and 0.11% $NTANa_3$ after the second extraction, 5.16% $IDANa_2$ (corresponding to 41.5 g IDAN) and 0.16% $NTANa_3$ after the third extraction, and 5.50% $IDANa_2$ (corresponding to 44.3 g IDAN) and 0.30% $NTANa_3$ after the fourth extraction.

The recovery of IDAN, as determined by analysis of the primary liquor (i.e., 49.3 g−4.6 g=44.7 g removed) agreed very well with the amount of $IDANa_2$ actually recovered (i.e., 44.3 g, reported as IDAN, present in the NaOH solution).

The IDAN primary liquor which had been extracted four times with methylene chloride was heated in a distillation apparatus to azeotropically distill any dissolved methylene chloride (bp, 38° C.); this distillation was continued until the vapor temperature reached 98° C. The solubility of methylene chloride was found to be about 0.8% (corresponding to 13 g of methylene chloride in 1650 g of extracted liquor).

The $IDANa_2$-containing caustic soda solution was also heated in a distillation apparatus in an attempt to remove and recover any methylene chloride dissolved therein; however, none distilled off. An analysis of the alkaline solution for chloride ion showed 971 parts per million which corresponds to 1.7 g methylene chloride. The chloride ion resulted from the hydrolysis of methylene chloride to sodium chloride and formaldehyde.

The term "extracting" as used herein means transferring a material from one solvent system to another solvent system via liquid-liquid extraction (i.e., by "liquid extraction" which, as noted supra, is also known as "solvent extraction").

As used herein:

IDAN means iminodiacetonitrile.

$IDAM_2$ means an alkali metal salt (i.e., a dialkali metal salt) of iminodiacetic acid; thus, where the alkali metal is sodium, the salt will be disodium iminodiacetate, "$IDANa_2$" and where the alkali metal is potassium the salt will be dipotassium iminodiacetate, "$IDAK_2$".

"IDA" means iminodiacetic acid.

"NTAN" means nitrilotriacetonitrile.

"NTANa₃" means trisodium nitrilotriacetonitrile.

The term "percent" ("%") means parts per hundred by weight unless otherwise defined where used.

Since methylene chloride is substantially insoluble in the aqueous systems (aqueous solutions of IDAN and aqueous alkali metal hydroxide which can contain IDAM$_2$) used in this process, the methylene chloride and the aqueous systems can be readily separated because, on standing for a few minutes they form two separate and distinct phases—a methylene chloride phase on the bottom and an aqueous phase on the top. For example, the bottom phase can be drawn off leaving the aqueous phase behind or the top phase can be pumped off leaving the methylene chloride phase behind. If difficulty in separating the phases is encountered, the addition of water can be used to induce separation. The added water will lower the density of the aqueous phase to induce the formation of said separate and distinct layers or phases.

Each extraction (i.e., the first extraction as described in Embodiment A and the second extraction as described in said embodiment) can be conducted at atmospheric pressure (i.e., 760 Tor) or at reduced pressure (i.e., pressure below atmospheric) or at elevated pressure (i.e., pressure above atmospheric). Said first and second extractions need not be conducted at the same pressure. At about atmospheric pressure each of said extractions can be conducted at about 2°–40° C., or 5°–35° C., or 10°–30° C., and said first and second extractions need not be conducted at the same temperature. Because of our disclosure, other operable temperatures and pressures will be readily apparent to those skilled in the art.

As used herein, the term "room temperature" means about 20°–25° C.

I claim:

1. A process for recovering an aqueous solution of alkali metal salts of iminodiacetic acid from an aqueous solution wherein iminodiacetonitrile is present in an amount of from about 1 to about 5 percent by weight, said process comprising:
   (a) extracting the aqueous iminodiacetonitrile solution with methylene chloride in a first extraction to form a solution of iminodiacetonitrile in methylene chloride, wherein the temperature of the two liquid phases during the extraction is from about 0° to about 38° C., and the ratio by volume of the aqueous iminodiacetonitrile solution to methylene chloride is from about 1:0.1 to about 1:10;
   (b) separating the methylene chloride, which now contains a portion of the iminodiacetonitrile, from the resulting extracted aqueous iminodiacetonitrile solution;
   (c) extracting the solution of iminodiacetonitrile in the methylene chloride with an aqueous solution of an alkali metal hydroxide, having a concentration of 0.5–5 moles of alkali metal hydroxide per liter, in a second extraction to remove iminodiacetonitrile values from the methylene chloride and to form an aqueous solution of a dialkali metal salt of iminodiacetonitrile; wherein the ratio by volume of the aqueous alkali metal hydroxide to the methylene chloride/iminodiacetonitrile solution is from about 1:0.1 to 1:10, and wherein the contact time between said solutions is about 0.1–20 minutes and the mole ratio of alkali metal hydroxide to iminodiacetonitrile present in the methylene chloride solution is at least 1;
   (d) separating the aqueous solution of dialkali salt of iminodiacetic acid from the resulting extracted methylene chloride said aqueous solution being essentially free of methylene chloride; and
   (e) concurrently with steps (a)–(d) above, subjecting the extracted aqueous solution of step (a) to azeotropic distillation to remove methylene chloride therefrom.

2. The process of claim 1 in which the aqueous solution of dialkali metal iminodiacetate is treated with sulfuric acid or hydrochloric acid to convert the dialkali metal iminodiacetate to iminodiacetic acid which precipitates and is recovered.

3. The process of claim 2 in which the acid is sulfuric acid.

4. The process of claim 1 in which the aqueous alkali metal hydroxide solution is sodium hydroxide.

* * * * *